United States Patent [19]
Cook et al.

[11] Patent Number: 5,814,663
[45] Date of Patent: Sep. 29, 1998

[54] METHOD FOR MAINTAINING AN EXISTING LEVEL OF BODY FAT

[75] Inventors: Mark E. Cook; Michael W. Pariza, both of Madison, Wis.

[73] Assignee: Wisconsin Alumni Research Foundation, Madison, Wis.

[21] Appl. No.: 736,562

[22] Filed: Aug. 28, 1996

Related U.S. Application Data

[63] Continuation-in-part of Ser. No. 297,472, Aug. 29, 1994, Pat. No. 5,554,646, and Ser. No. 659,845, Jun. 7, 1996.

[51] Int. Cl.$^6$ .................................................. A61K 31/20
[52] U.S. Cl. .......................................... 514/560; 514/558
[58] Field of Search ..................................... 514/560, 558

[56] References Cited

U.S. PATENT DOCUMENTS

| | | | |
|---|---|---|---|
| 4,603,142 | 7/1986 | Burger et al. | 514/456 |
| 4,868,001 | 9/1989 | Maruta | 425/623 |
| 5,017,614 | 5/1991 | Pariza et al. | 514/558 |
| 5,070,104 | 12/1991 | Pariza et al. | 514/549 |
| 5,162,337 | 11/1992 | Elbrecht et al. | 514/300 |
| 5,428,072 | 6/1995 | Cook et al. | 514/560 |
| 5,430,066 | 7/1995 | Cook | 514/558 |
| 5,554,646 | 9/1996 | Cook | 514/560 |

FOREIGN PATENT DOCUMENTS 61-216658  9/1986  Japan .

OTHER PUBLICATIONS

Journal of Nutrition, Harris, 1991 121(17) pp. 1109–1116 "Physiological Response of Mature Rats to Replacement of Dietary Fat With a Fat Substitute".

Y.L. Ha; N.K. Grimm and M.W. Pariza, *Carcinogenesis*, vol. 8, No. 12, pp. 1881–1887(1987).

Y.L. Ha; N.K. Grimm and M.W. Pariza, J. Agric. Food Chem., vol. 37, No. 1, pp. 75–81(1987).

M.W. Pariza, Food Research Institute 1988 Annual Fall Meeting, Oct. 12, 1988.

The Merck Index, Tenth Edition (1983), p. 790.

The Merck Veterinary Manual, Fifth Edition (1979), pp. 1340–1343 and 1374 and 1379.

*Primary Examiner*—Ceila Chang
*Assistant Examiner*—Jean F. Vollano
*Attorney, Agent, or Firm*—Quarles & Brady

[57] ABSTRACT

A method of maintaining an existing level of body fat or body weight in a human which comprises administering to a human desiring to maintain that existing level a safe and effective amount of conjugated linoleic acid (CLA) to maintain that level.

6 Claims, No Drawings

METHOD FOR MAINTAINING AN EXISTING LEVEL OF BODY FAT

RELATED CASE

The present application is a continuation-in-part of applications U.S. Ser. No. 08/297,472, filed Aug. 29, 1994, now U.S Pat. No. 5,554,646 and U.S. Ser. No. 08/659,845, filed Jun. 7, 1996.

FIELD OF THE INVENTION

The present invention generally relates to human nutrition. More particularly, it relates to a method of treating humans to maintain an existing level of body fat and/or body weight.

BACKGROUND OF THE INVENTION

There are a significant number of people, who are happy with their existing body weights and levels of body fat, but who do not want their weight or levels of body fat to increase. In addition, there are thousands of people who annually go on diets to lose body fat or weight. Unfortunately, most of those that are successful cannot maintain the lower levels of body fat and/or body weight which they have achieved.

There is a need for a method of maintaining an existing level of body fat and/or body weight in a human.

BRIEF SUMMARY OF THE INVENTION

It is an object of the present invention to disclose a method of maintaining an existing level of body fat and/or body weight in a human.

We have discovered that an existing level of body fat and/or body weight in a human can be maintained by administering to the human a safe and effective amount of an active form of a conjugated linoleic acid, such as 9,11-octadecadienoic acid and 10,12-octadecadienoic acid, an ester thereof, a non-toxic salt thereof, and mixtures thereof.

The terms "conjugated linoleic acids" and "CLA" as used herein are intended to include 9,11-octadecadienoic acid, 10,12-octadecadienoic acid and their active derivatives, such as non-toxic salts and esters, and mixtures thereof.

The method of the present invention can be used by ex-dieters to maintain the lower level of body fat and/or body weight they have achieved or by persons who wish to increase their fat intake without increasing their level of body fat and/or body weight.

It will be apparent to those skilled in the art that the forementioned objects and other advantages may be achieved by the practice of the present invention.

DESCRIPTION OF THE PREFERRED EMBODIMENT

The method of the present invention comprises administering to the human desirous of maintaining his or her existing level of body fat and/or body weight a safe and effective amount of an active form of a conjugated linoleic acid, which is selected from a conjugated linoleic acid, such as 9,11-octadecadienoic acid and 10,12-octadecadienoic acid, an ester thereof, a non-toxic salt thereof, and mixtures thereof.

The existing level of the human's body fat and/or body weight can be determined by a variety of methods. The body weight of a person can be obtained simply by weighing the person. One method of determining body fat simply comprises doing a "pinch test" at the waist, chest, thighs and other body parts. Another more sophisticated method, which is commonly used for athletes, involves completely submerging the person in liquid and calculating the body weight under water.

The amount of the CLA to be administered normally is an amount which is equal to about 1% to about 30% of the fat in the human's diet. If the CLA is taken in pharmaceutical dosage form the dose will normally be about 100 mg. to 20,000 mg. per day of CLA in the form of the free acids. Since the CLA is a natural food ingredient and relatively non-toxic, the amount which can be consumed is not critical as long as it is enough to be effective and it is not contraindicated because of the human's health.

The practice of the present invention is further illustrated by the examples which follow:

EXAMPLE 1

Synthesis Of Conjugated Lionoleic Acids (CLA) From Linoleic Acid And Safflower Oil Ethylene glycol (1000 g) and 500 g potassium hydroxide (KOH) are put into a 4-neck round bottom flask (5000 ml). The flask is equipped with a mechanical stirrer, a thermometer, a reflux condenser, and a nitrogen inlet. (The nitrogen introduced in first run through two oxygen traps).

Nitrogen is bubbled into the ethylene glycol and KOH mixture for 20 min and the temperature is then raised to 180° C.

1000 g of linoleic acid, corn oil, or safflower oil is then introduced into the flask. The mixture is heated at 180° C. under an inert atmosphere for 2.5 hours.

The reaction mixture is cooled to ambient conditions and 600 ml Hcl is added to the mixture which is stirred for 15 min. The Ph of the mixture is adjusted to Ph 3. Next, 200 ml of water is added into the mixture and stirred for 5 min. The mixture is transferred into a 5 L separatory funnel and extracted three times with 500-ml portions of hexane.

The aqueous layer is drained and the combined hexane solution extracted with four 250-ml portions of 5% NaCl solution.

The hexane is washed 3 times with water. The hexane is transferred to a flask and the moisture in the hexane removed with anhydrous sodium sulfate ($Na^2$ $SO^4$). The hexane is filtered through Whatman paper into a clean 1000 ml round bottom flask and the hexane removed under vacuum with a rotoevaporator to obtain the CLA. The CLA is stored in a dark bottle under argon at −80° C. until time of use.

This method can be modified so as to utilize only food-grade reagents and solvents as listed in *Food Chemicals Codex*, fourth edition, Institute of Medicine, National Academy Press, 1996.

The active forms of CLA include, in addition to the free acids, the non-toxic salts thereof, the active esters thereof, such as triglycerides, and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987). The free acid forms of the CLA may be prepared by isomerizing linoleic acid. The non-toxic salts of the free acids may be made by reacting the free acids with a non-toxic base.

One method of synthesizing CLA is described in Example 1. However, CLA may also be prepared from linoleic acid by the action of a linoleic acid isomerase from a harmless microorganism, such as the Rumen bacterium *Butyrivibrio fibrisolvens*. Harmless microorganisms in the intestinal tracts of rats and other monogastric animals may also convert linoleic acid to CLA (S. F. Chin, J. M. Storkson, W. Liu, K. Allbright and M. W. Pariza, 1994, J. Nutr. 124; 694–701.

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a Ph of about 8 to 9. CLA also can be esterified to glycerol to form mono-, di-, and triglycerides.

Theoretically, 8 possible geometric isomers of 9,11- and 10,12-octadecadienoic acid (c9, c11; c9,t11;t9,c11; t9,2t11; c10,c12; c10,t12;t10,c12 and t10,t12) would form from the isomerization of c9,c12-octadecadienoic acid. As a result of the isomerization,. only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9, c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The exact amount of CLA to be administered to a human to maintain a level of body fat, of course, can depend upon the food the human consumes, the form of CLA employed, and the route of administration. It also can depend upon the isomer ratios. However, generally the amount administered will be the equivalent of about 1% to about 30% of the weight of the fat in the human's diet.

The CLA can be administered in food or as pharmaceutical compositions containing the CLA as a free acid; a salt thereof; an ester thereof, such as a triglyceride; or mixtures thereof.

The amount of CLA to be administered can be expressed as the amount of CLA based on the total calories consumed daily by the patient e.g. 0.03 to 3 gram CLA per 100 calories. Alternatively, the amount of CLA can be expressed as a percentage of the lipid or fat in the food, such as 0.3% to 100% of the food lipid, or as an amount of CLA per gram of food lipid, such as 3 to 1000 mg. CLA per gram of lipid consumed by the patient.

Generally, the amount of CLA to be administered in pharmaceutical dosage form will normally be about 100 mg. to about 20,000 mg. of CLA in the form of the free acids per day. However, the upper limit of the amount to be employed is not critical because CLA is relatively non-toxic.

The CLA and its non-toxic derivatives, such as the non-toxic salts, in addition to being added to an animal's food can be administered in the form of pharmaceutical compositions, such as tablets, wafer, capsules, solutions or emulsions to the humans.

The preferred pharmaceutical compositions of CLA contain the non-toxic sodium, potassium or calcium salt of CLA in combination with a pharmaceutical diluent. When the compositions are solutions or suspensions intended for oral administration, the diluent will be one or more liquid diluents. When the product is a tablet or capsule, other conventional diluents, such as lactose, can be employed.

Examples 2 to 4 describe representative foods containing added CLA.

EXAMPLE 2

A liquid preparation for parenteral administration to humans contains emulsified fat particles of about 0.33–0.5 $\mu$m in diameter. In addition, the emulsions can contain Water for Injection USP as a diluent, egg phosphatides (1–2%) as an emulsifying agent and glycerin (2–3%) to adjust toxicity. These emulsions can be infused intravenously to patients requiring parenteral nutrition. A preparation for use in the present invention would contain the same ingredients plus 0.5 mg/gm to 10 mg/gm of CLA or alternatively, 0.3% to 100% CLA based on the food lipid or 0.03 gram to 3 gram per 100 calorie serving. For such parenteral foods the CLA usually should be present in the form of the triglycerides.

EXAMPLE 3

A dietetic margarine for use in the present invention is a semi-solid or solid vegetable oil-based margarine which, in addition to the usual ingredients, contains CLA. Such a margarine will contain about 0.25 mg/gram to about 800 mg/gm of CLA or about 0.003 gram to 9 gm CLA per 100 calorie serving.

EXAMPLE 4

A low residue liquid enteral dietetic product useful as a high-protein, vitamin and mineral supplement contains added CLA. The amount of CLA present can be about 0.05% to about 5% by weight of the product or about 0.3% to about 100% of the lipid present or about 0.03 to 3 gram CLA per 100 calories.

One serving (140 calories) of a representative formula can contain the following:

| | |
|---|---|
| Protein (egg white solids) | 7.5 g |
| Fat (CLA) | 0.1 g |
| Carbohydrate | 27.3 g |
| (sucrose, hydrolyzed corn starch) | |
| Water | 1.9 g |
| Vitamins and Minerals (RDA amounts) | |

It will be readily apparent to those skilled in the art that many other foods, including those described in U.S. Pat. Nos. 4,282,265 and 5,470,839, can be prepared by adding CLA to the food or by replacing some of the fat in the food with CLA.

The following examples illustrate the practice of the method of the present invention.

EXAMPLE 5

The level of body fat of a 168 pound, healthy human male, age 40 was determined using the "pinch test" on his waist, thighs and upper arms and his weight was determined by weighing on a scale. He then was administered 4 capsules (2400 mg of CLA as the fatty acids) daily and permitted to consume an unrestricted diet. After 8 weeks it was determined that his weight (165 pounds) and body fat level had stabilized at lower levels on an unrestricted diet. CLA consumption was stopped for 1 week while food consumption was unrestricted. After the 1 week period he was weighed and it was found that 3 pounds of body weight had been gained. The administration of CLA at the original dosage was resumed for 7 weeks whereupon the body weight and body fat levels returned to the lower levels previously reached after the initial 8 weeks of administration of CLA. In the past, he had normally gained weight and body fat on an unrestricted diet. Similar results were obtained in several other humans.

EXAMPLE 6

A healthy 210 pound male human, age 53, consumed 1200 mg CLA per day for three weeks. During this time his appetite was somewhat diminished. He then increased his CLA intake to 2400 mg per day and noted a further decrease in appetite. Throughout this time he did not lose body weight but noted a decrease in body fat as evidenced by the "pinch" test.

EXAMPLE 7

A healthy 174 pound female, age 53, consumed 1200 mg CLA per day. Within three weeks she had lost 3 pounds, her waistline had decreased by about 1.5–2 inches, and her appetite had diminished. She continued taking CLA at the same dose level for three more weeks during which time her body weight and waistline remained stabilized.

It also will be readily apparent to those skilled in the art that a number of modifications or changes may be made without departing from the spirit and scope of the present invention. Therefore, the invention is only to be limited by the claims.

We claim:

1. A method of treating a human to maintain a level of body fat of the human at an existing level, said method comprising administering to said human about 100 milligrams to about 20,000 milligrams of conjugated linoleic acid per day.

2. A method of claim 1 in which the conjugated, linoleic acid is administered in a food containing added conjugated linoleic acid.

3. A method of claim 1 in which the conjugated linoleic acid is 9,11-octadecadienoic acid.

4. A method of claim 1 in which the conjugated linoleic acid is 10,12-octadienoic acid.

5. A method of claim 1 in which the conjugated linoleic acid is in the form of a non-toxic salt of a conjugated linoleic acid.

6. A method of claim 1 in which the conjugated linoleic acid is in the form of a triglyceride of a conjugated linoleic acid.

* * * * *